(12) United States Patent
Khanuja et al.

(10) Patent No.: US 7,510,836 B2
(45) Date of Patent: Mar. 31, 2009

(54) ALPHA ARTEETHER RESISTANCE DOMAIN

(75) Inventors: Suman Preet Singh Khanuja, Lucknow (IN); Suchi Srivastava, Lucknow (IN); Ajit Kumar Shasany, Lucknow (IN); Tiruppadiripuliyur Ranganathan Santha Kumar, Lucknow (IN); Mahendra Pandurang Darokar, Lucknow (IN); Preeti Chand, Lucknow (IN); Sushil Kumar, Lucknow (IN)

(73) Assignee: Council of Scientific & Industrial Research, New Delhi (IN)

( * ) Notice: Subject to any disclaimer, the term of this patent is extended or adjusted under 35 U.S.C. 154(b) by 121 days.

(21) Appl. No.: 10/809,814

(22) Filed: Mar. 26, 2004

(65) Prior Publication Data

US 2005/0048532 A1 Mar. 3, 2005

Related U.S. Application Data

(60) Provisional application No. 60/458,376, filed on Mar. 31, 2003.

(51) Int. Cl.
*C12Q 1/68* (2006.01)
(52) U.S. Cl. .................... 435/6; 435/91.1; 435/91.2
(58) Field of Classification Search .................... None
See application file for complete search history.

(56) References Cited

U.S. PATENT DOCUMENTS

| | | | |
|---|---|---|---|
| 6,127,405 A | 10/2000 | Kumar et al. | |
| 6,423,741 B1 | 7/2002 | Khanuja et al. | |

OTHER PUBLICATIONS

Yoshida et al. Mol. Gen. Genetics vol. 211:1-7. 1988.*

* cited by examiner

*Primary Examiner*—Gary Benzion
*Assistant Examiner*—Heather G Calamita
(74) *Attorney, Agent, or Firm*—Dinesh Agarwal, P.C.

(57) ABSTRACT

The present invention relates to an alpha-arteether resistance domain (ADR) of Sequence ID No.1 and a method of identifying ADR in alpha-arteether resistant pathogens and lastly, it relates to set three pairs of primers of sequence ID Nos. 3 to 8.

1 Claim, No Drawings

SEQUENCE LISTING

<160> NUMBER OF SEQ ID NOS: 9

<210> SEQ ID NO 1
<211> LENGTH: 21
<212> TYPE: DNA
<213> ORGANISM: Escherichia coli

<400> SEQUENCE: 1
ggtgactcgg cggtctatga c                                              21

<210> SEQ ID NO 2
<211> LENGTH: 7
<212> TYPE: PRT
<213> ORGANISM: Escherichia coli

<400> SEQUENCE: 2

Gly Asp Ser Ala Val Tyr Asp
1               5

<210> SEQ ID NO 3
<211> LENGTH: 21
<212> TYPE: DNA
<213> ORGANISM: Artificial Sequence
<220> FEATURE:
<223> OTHER INFORMATION: A forward primer for amplifying gyrase A gene

<400> SEQUENCE: 3
aatttgcgac ctttgaatcc g                                              21

<210> SEQ ID NO 4
<211> LENGTH: 22
<212> TYPE: DNA
<213> ORGANISM: Artificial Sequence
<220> FEATURE:
<223> OTHER INFORMATION: A reverse primer for amplifying gyrase A gene

<400> SEQUENCE: 4
ctgggtctgg gagtagaggt tg                                             22

<210> SEQ ID NO 5
<211> LENGTH: 22
<212> TYPE: DNA
<213> ORGANISM: Artificial Sequence
<220> FEATURE:
<223> OTHER INFORMATION: A forward primer for amplifying gyrase A gene

<400> SEQUENCE: 5
atgcggtcgg tgaagttgtg ct                                             22

<210> SEQ ID NO 6
<211> LENGTH: 22
<212> TYPE: DNA
<213> ORGANISM: Artificial Sequence
<220> FEATURE:
<223> OTHER INFORMATION: A reverse primer for amplifying gyrase A gene

<400> SEQUENCE: 6
caaactcggt cactggcagg at                                             22

<210> SEQ ID NO 7
<211> LENGTH: 20
<212> TYPE: DNA
<213> ORGANISM: Artificial Sequence
<220> FEATURE:

<223> OTHER INFORMATION: A forward primer for amplifying gyrase A gene

<400> SEQUENCE: 7
tgccgctgga gcaggacgaa                                              20

<210> SEQ ID NO 8
<211> LENGTH: 20
<212> TYPE: DNA
<213> ORGANISM: Artificial Sequence
<220> FEATURE:
<223> OTHER INFORMATION: A reverse primer for amplifying gyrase A gene

<400> SEQUENCE: 8
tcaattcaaa caagggagat                                              20

<210> SEQ ID NO 9
<211> LENGTH: 3066
<212> TYPE: DNA
<213> ORGANISM: Escherichia coli

<400> SEQUENCE: 9
tggcaagaca aacgagtata tcaggcattg gatgtgaata aagcgtatag gtttacctca      60
aactgcgcgg ctgtgttata atttgcgacc tttgaatccg ggatacagta gagggatagc     120
ggttagatga gcgaccttgc gagagaaatt acaccggtca acattgagga agagctgaag     180
agctcctatc tggattatgc gatgtcggtc attgttggcc gtgcgctgcc agatgtccga     240
gatggcctga gccggtaca ccgtcgcgta ctttacgcca tgaacgtact aggcaatgac      300
tggaacaaag cctataaaaa atctgcccgt gtcgttggtg acgtaatcgg taaataccat     360
ccccatggtg actcggcggt ctatgacacg attgtccgca tggcgcagcc attctcgctg     420
cgttatatgc tggtagacgg tcagggtaac ttcggttcta tcgacggcga ctctgcggcg     480
gcaatgcgtt atacggaaat ccgtctggcg aaaattgccc atgaactgat ggccgatctc     540 gaaaagaga cggtcgattt cgttgataac tatgacggca cggaaaaaat tccggacgtc      600
atgccaacca aaattcctaa cctgctggtg aacggttctt ccggtatcgc cgtaggtatg     660
gcaaccaaca tcccgccgca caacctgacg gaagtcatca acggttgtct ggcgtatatt     720
gatgatgaag acatcagcat tgaagggctg atggaacaca tcccggggcc ggacttcccg     780
acggcggcaa tcattaacgg tcgtcgcggt attgaagaag cttaccgtac cggtcgcggc     840
aaggtgtata tccgcgctcg cgcagaagtg gaagttgacg ccaaaaccgg tcgtgaaacc     900
attatcgtcc acgaaattcc gtatcaggta acaaagcgc cctgatcga aagattgcg       960 gaactggtaa agaaaaaacg cgtggaaggc atcagcgcgc tgcgtgacga gtctgacaaa    1020
gacggtatgc gcatcgtgat tgaagtgaaa cgcgatgcgg tcggtgaagt tgtgctcaac    1080
aacctctact cccagaccca gttgcaggtt tctttcggta tcaacatggt ggcattgcac    1140
catggtcagc cgaagatcat gaacctgaaa gacatcatcg cggcgtttgt tcgtcaccgc    1200
cgtgaagtgg tgacccgtcg tactatttc gaactgcgta aagctcgcga tcgtgctcat    1260
atccttgaag cattagccgt ggcgctggcg aacatcgacc cgatcatcga actgatccgt    1320
catgcgccga cgcctgcaga agcgaaaact gcgctggttg ctaatccgtg gcagctgggc    1380
aacgttgccg cgatgctcga acgtgctggc gacgatgctc gcgtccgga atggctggag    1440 ccagagttcg gcgtgcgtga tggtctgtac tacctgaccg aacagcaagc tcaggcgatt    1500
ctggatctgc gtttgcagaa actgaccggt cttgagcacg aaaaactgct cgacgaatac    1560
aaagagctgc tggatcagat cgcggaactg ttgcgtattc ttggtagcgc cgatcgtctg    1620

```
atggaagtga tccgtgaaga gctggagctg gttcgtgaac agttcggtga caaacgtcgt    1680
actgaaatca ccgccaacag cgcagacatc aacctggaag atctgatcac ccaggaagat    1740
gtggtcgtga cgctctctca ccagggctac gttaagtatc agccgctttc tgaatacgaa    1800
gcgcagcgtc gtggcgggaa aggtaaatct gccgcacgta ttaaagaaga agactttatc    1860
gaccgactgc tggtggcgaa cactcacgac catattctgt gcttctccag ccgtggtcgc    1920
gtctattcga tgaaagttta tcagttgccg gaagccactc gtggcgcgcg cggtcgtccg    1980
atcgtcaacc tgctgccgct ggagcaggac gaacgtatca ctgcgatcct gccagtgacc    2040
gagtttgaag aaggcgtgaa agtcttcatg gcgaccgcta acggtaccgt gaagaaaact    2100
gtcctcaccg agttcaaccg tctgcgtacc gccggtaaag tggcgatcaa actggttgac    2160
ggcgatgagc tgatcggcgt tgacctgacc agcggcgaag acgaagtaat gctgttctcc    2220
gctgaaggta aagtggtgcg ctttaaagag tcttctgtcc gtgcgatggg ctgcaacacc    2280
accggtgttc gcggtattcg cttaggtgaa ggcgataaag tcgtctctct gatcgtgcct    2340
cgtggcgatg gcgcaatcct caccgcaacg caaaacggtt acggtaaacg taccgcagtg    2400
gcggaatacc caaccaagtc gcgtgcgacg aaaggggtta tctccatcaa ggttaccgaa    2460
cgtaacggtt tagttgttgg cgcggtacag gtagatgact gcgaccagat catgatgatc    2520
accgatgccg gtacgctggt acgtactcgc gtttcggaaa tcagcatcgt gggccgtaac    2580
acccagggcg tgatcctcat ccgtactgcg gaagatgaaa acgtagtggg tctgcaacgt    2640
gttgctgaac cggttgacga ggaagatctg gataccatcg acggcagtgc cgcggaaggg    2700
gacgatgaaa tcgctccgga agtggacgtt gacgacgagc cagaagaaga ataattttac    2760
ttcttcatgc caaaagggag ctatctccct tgtttgaatt gaaaagtcca ggctgcaaag    2820
tctgggcttt tgtcgtatta gggcacggta agtttggct gtgcccgtaa aaaatggctg    2880
gctatacaca aggaatgtgg caatgagtgg tgaaaaaaag gcgaaaggct ggcggttcta    2940
tggtcttgta ggttttggcg caatagcact gctttccgct ggcgtctggg cgttgcaata    3000
tgctggcagt gggccagaaa aaacgttgtc gccgctggtg gtgcacaaca atctgcaaat    3060
cgatct                                                                3066
```

ALPHA ARTEETHER RESISTANCE DOMAIN

CROSS-REFERENCE TO RELATED APPLICATIONS

The present application claims priority on prior U.S. Provisional Application Ser. No. 60/458,376, filed Mar. 31, 2003, which is incorporated herein in its entirety by reference.

REFERENCE TO SEQUENCE LISTING

The present application incorporates by reference a file named: US 1374-04 Khanuja Sequence Listing including SEQ ID NO.: 1 to SEQ ID NO.: 9, provided herewith in a computer readable form—on a diskette, created on Nov. 5, 2004 and containing 5,993 bytes. The sequence listing information recorded on the diskette is identical to the written (on paper) sequence listing provided herein.

FIELD OF THE PRESENT INVENTION

The invention relates to a sequence of nucleotides in the DNA of *Escherichia coli* gyrase A gene which when changed provides resistance to cc-arteether to the bacteria. This sequence can also be defined as the a-arteether resistance domain and can have wide spread application in the detection of resistance to a-arteether and related seauiterpene endoperoxides. This invention also relates to the functional domain of gyrase A protein and in future can be utilized in structure/target based drug designing.

BACKGROUND AND PRIOR ART REFERENCES OF THE INVENTION

Since, ancient times, the plant *Artemisia annua* (family: Asteraceae) has been used as a traditional Chinese herbal medicine known as Qinghao for treating fever and malaria. The effective constituent was isolated by the Chinese investigators in 1972 and shown to be the sesquiterpene lactone, named artemisinin or qinghaosu (Jing-Ming et al., 1979; Tu et <2/.,1981).The structure of artemisinin has now been confirmed by a variety of analytical methods. Because artemisinin posseses high plasmodicidal property, it holds considerable promise for the treatment of drug resistant malaria. Artemisinin is poorly soluble in water and oil but readily soluble in most aprotic solvents. This property coupled with its short half-life, as well as desire to improve more potent derivatives, led to the efforts for chemically modifying its structure and synthesizing new artemisinin derivatives. Thus, ether derivatives of artemisinin called arteethers were prepared from dihydroartemisinin by etherification with ethanol in the presence of Lewis acid.

Absolute stereochemistry of arteethers (a and 6 isomers) at C-12 was also determined and it is 2-3 times more potent than artemisinin. The compounds a and 8 arteethers were developed as an antimalarial drug in India by the Central Institute of Medicinal and Aromatic Plants (CIMAP) and Central Drug Research Institute (CDRI) after phase III clinical trials. The arteether is presently sold in the market under the trade name E-MAL (injection).

In our earlier invention, we found a novel selective property of the compound a-arteether, which is inhibitory against the gyr mutant strains of *E.coli*, but ineffective against wild type strains (U.S. Pat. No. 6,127,405). Further we also developed in a separate U.S. Pat. No. 6,423,741 a strategic and novel combinations of a arteether which can be used as advanced generation drug(s) to counter the resistance development itself while, having a potential to be used in treating infectious diseases particularly in those cases where drug resistant strains are known to appear very frequently.

The uniqueness and most useful feature is that, in a combination of a arteether and quinolone drugs and likewise, the spontaneous mutants arising resistant to quinolones or the derivatives will be killed by a arteether and at the same time any a arteether resistant strains become highly sensitive to nalidixic acid and hence eliminated by it through the combination approach. The new composition of compounds inhibits the resistance development due to mutation in the gyr A gene of bacteria, in which one component is a arteether and the other may be nalidixic acid or any of the fluoroquinolones (comprising of Ciprofloxacin, Norfloxacin, Levofloxacin, Sparfloxacin, Oxfloxacin and Lomefloxacin etc.) or compounds of similar nature against which the resistance may develop through a related process.

These above inventions were based on in vivo assays and do not indicate any insight into the genome for a arteether resistance mechanism based on which similar molecules can be structured/designed to target the DNA gyrase enzyme. Person skilled in the art may obtain clues from the present invention to design such molecules for a wide spectrum of microbes and hence the commercial importance of the invention.

OBJECTS OF THE PRESENT INVENTION

The main object of the present invention is to identify an alpha-arteether resistance domain.

Another main object of the present invention is to develop a method of identifying an alpha-arteether resistance domain in a pathogen.

SUMMARY OF THE PRESENT INVENTION

The invention relates to a sequence of nucleotides in the DNA of *Escherichia coli* gyrase A gene which when changed provides resistance to cc-arteether to the bacteria. This sequence can also be defined as the a-arteether resistance domain and can have wide spread application in the detection of resistance to a-arteether and related seauiterpene endoperoxides. This invention also relates to the functional domain of gyrase A protein and in future can be utilized in structure/target based drug designing.

DETAILED DESCRIPTION

Accordingly, the present invention relates to identifying an alpha-arteether resistance domain, and also, to developing a method of identifying an alpha-arteether resistance domain in a pathogen and thereby help in developing drugs against the pathogens.

In main embodiment of the present invention, wherein an oligonucleotide as alpha-arteether resistance domain (ADR) GGTCACTCGGCGGTCTATGAC of SEQ ID No. 1.

In still another embodiment of the present invention, wherein the domain is from 241 to 261 nucleotide position of gyr A gene from translation start site of *E. Coli.*

In still another embodiment of the present invention, wherein an oligopeptide Gly Asp Ser Ala Val Tyr Asp of SEQ ID No. 2, corresponding to an oligonucleotide as alpha-arteether resistance domain (ADR) of SEQ ID No. 1.

In still another embodiment of the present invention, wherein the oligopeptide is from amino acid position 81 to 87 in gyrase A peptide of the enzyme.

In still another embodiment of the present invention, wherein a method of identifying alpha-arteether resistance domain (ADR) in a alpha-arteether resistant pathogens, to help develop drugs against the pathogen, said method comprising steps of:

developing alpha-arteether resistant mutant from arteether sensitive strain,
  identifying both phenotypic and genotypic characteristics of the developed alpha-arteether resistant mutant, and
  identifying alpha-arteether resistance domain (ADR) in an alpha-arteether resistant pathogens.

In still another embodiment of the present invention, wherein an alpha-arteether resistance domain (ADR) is an oligonucleotide of SEQ ID No. 1

In still another embodiment of the present invention, wherein the ADR is from 241 to 261 nucleotide position of gyr A gene from translation start site of E. Coli.

In still another embodiment of the present invention, wherein the ADR has corresponding an oligopeptide of SEQ ID No. 2.

In still another embodiment of the present invention, wherein the oligopeptide is from amino acid position 81 to 87 in gyrase A peptide of the enzyme.

In still another embodiment of the present invention, wherein a set of three pairs of primers of SEQ ID Nos. 3, 4; 5, 6; and 7, 8.

In still another embodiment of the present invention, wherein the primers of SEQ ID Nos 3, 5, and 7 are forward primers.

In still another embodiment of the present invention, wherein the primers of SEQ ID Nos 4, 6, and 8 are reverse primers.

The next millenium will visualize a serious problem of antibiotic resistance for the antibiotics developed during the previous century and this is classified as a serious threat in the WHO report on infectious diseases. Currently antibiotics provide the main basis of causative therapy of bacterial infections. However high genetic variability of bacteria enable them to rapidly evade the action of antibiotics by developing resistance. Thus there has been a continuous search for new and potent antibiotics. The group of fluoroquinolones thus are vulnerable to this phenomena and our emphasis is to search new antibiotic from plant sources. In this context we have invented the semisynthetic compound ct-arteether and its effect on fluoroquinolone resistant bacteria (U.S. Pat. No. 6,127,405). The patent (U.S. Pat. No. 6,127,405) deals with the resistance developed against quinolone drugs and use of a-arteether to control the infections, but does not speak about the resistance development against a-arteether itself. The inventors studied this aspect of resistance development and experimentally proved that this cross-resistance (quinolone vs arteether) development can be taken care of using the Combination therapy, which is not invented in the earlier invention (U.S. Pat. No. 6,423,741). As the invention of a-arteether as a agent to kill the quinolone resistant bacteria is new, no one knows about the resistance developing from a-arteether. This led us to the invention of the drug resistance prevention system using a-arteether and a fluoroquinolone drug. We studied at the DNA level to determine the mutations developed in the gyrase A gene of bacteria *Escherichia coli* (Kumar, S. 1976. Journal of Bacteriology, 125: 545-555.). This we assumed as the bacteria developed resistance against fluoroquinolones are sensitive to a-arteether and the bacteria resistant to a-arteether are resistant to fluoroquinolones. The fluoroquinolone drugs induce mutation in the gyrase A gene of bacteria and thereby the resistance developed.

There are consistent attempts to determine the mechanism of action of the antibiotics and based on which the newer antibiotics are designed by chemical modification of the prototype compounds. Simultaneously, attempts are being made to follow genomic approaches using the genomic database and identifying lethal targets. So, new drugs of fluoroquinolones group were developed to target bacterial type II topoisomerases which are otherwise known as DNA gyrases. Topoisomerases play an essential role for the control of the three-dimentional DNA structure in all cells. Among all topoisomerases bacterial type II topoisomerase (DNA gyrase) is unique by its ability to introduce the negative supercoils into covalently closed circular double stranded DNA in the relaxed state. DNA gyrase enzyme has two sub-units A and B. The quinolones and fluoroquinolones are targeted to the A subunit of the enzyme and shows bactericidal activity against dividing cells. This is due to the inhibition of the replicative DNA synthesis rather than the protein or RNA synthesis.

In our experiments planned to detect the biological activity of arteethers against various strains of *E.coli*, we found an interesting feature that among the two isomers, only a isomer of arteether is able to inhibit the growth of a particular *E.coli* strain DH5a available commercially, which carries a well defined mutation (gyrA 96) in the gene encoding DNA gyrase-A enzyme subunit. As a result of this mutation, the said strain is also resistant to a drug called nalidixic acid. The other *E.coli* strains which do not carry gyr mutation were invariably resistant to a-arteether.

To ascertain the involvement of gyrA mutation, another *E.coli* strain NK 5819 which is also GyrA" and nalidixic acid resistant was tested for arteether sensitivity. As expected, strain NK5819 was also sensitive only to a-isomer of arteether. For further substantiating the Gyr" and a-arteether resistant relationship in *E.coli*, yet another strain MTCC 482 defective in DNA gyrase B subunit and hence termed GyrB" was also^ tested for arteether sensitivity. Interestingly, even the gyrB MTCC 482 strain was susceptible only to a-isomer of arteether. The assays for arteether sensitivity was performed by the standard single disk diffusion method (Bauer et al, 1966). As a next step, we isolated gyrA mutants of *E.coli* strain CA 8000, which is otherwise Gyr+ and nalidixic acid sensitive. The gyrA mutants of CA8000 were isolated as nalidixic acid resistant colonies (20 ug/ml), after mutagenic treatment with NTG (100 Hg/ml). The isolated CA8000 gyrA mutants were also sensitive only to a isomer of arteether. The above experiments clearly demonstrated the stereospecific inhibition of gyr mutants of *E.coli* by a-arteether. On the other hand, none of the above described gyr mutants were sensitive to the fl-isomer. To define precisely the involvement of gyr genes only in the a-arteether sensitivity, we utilised two recombinant clones (pMK 90 and pMK47 containing functional gyr A and gyrB genes respectively) in trans-complementation assays. For this purpose, we mobilized the plasmid clones into the *E.coli* gyr mutant strains. The resulting transformants were now nalidixic acid sensitive and a-arteether resistant. This constituted the direct evidence supporting our observation that DNA gyrase enzyme alone is involved in conferring a-arteether sensitivity to *E.coli* strain. Hence, the gyr strains of *E.coli* can be used as a biological sensor for detecting the a-isomer of arteether. DNA gyrase enzyme is essential for the bacterial growth. This enzyme transiently breaks the DNA strands and introduces negative superhelical turns in an ATP-dependent process. The *E.coli* DNA gyrase enzyme is a tetramer with two subunits A and B. These two subunits are nalidixic acid and coumermycin sensitive respectively (U.S. Pat. No. 6,127,405 and a co-pending patent).

The genes (gyrA and gyrB } encoding both these subunits have been isolated and cloned in E. coli and the prior arts define the drug resistance domain in gyr A gene for quinolones and fluoroquinolones. But the prior arts don't describe the resistance domains for a-arteether.

Quinolone Resistance Determining Region

Sequence analysis to DNA from many Bacterial species shows that resistance mutation tend to alter amino acid near the putative active site in the gyr A protein (Tyr 122 in E.coli). This region extending between amino acid 67 to 106 is called the QRDR within gyr A of E.coli. Mutations of two codons Serine 83 to a hydrophobic amino acid generally confers more resistance than does mutation at position 87.

So in planned experiments we screened and isolated several gyr A spontaneous mutants resistant to a-arteether from the a-arteether sensitive strains. These a-arteether sensitive strains were selected randomly from the quinolone and fluoroquinolone resistant strains. From the genebank database the gyr A gene sequence for *Escherichia coli* was downloaded and forward and reverse primers were designed and synthesized in ABI 392 DNA synthesizer.

The gyrase A gene of *Escherichia coli* and the primer sites.

```
           TGGCAAGACA AACGAGTATA TCAGGCATTG GATGTGAATA AAGCGTATAG        -77

GTTTACCTCA AACTGCGCGG CTGTGTTATA ATTTGCGACC TTTGAATCCG        -27

Forward -1                  5' A ATTTGCGACC TTTGAATCCG 3'
                                      +1

GGATACAGTA GAGGGATAGC GGTTAGATGA GCGACCTTGC GAGAGAAATT        +24

ACACCGGTCA ACATTGAGGA AGAGCTGAAG AGCTCCTATC TGGATTATGC        +74

GATGTCGGTC ATTGTTGGCC GTGCGCTGCC AGATGTCCGA GATGGCCTGA       +124

AGCCGGTACA CCGTCGCGTA CTTTACGCCA TGAACGTACT AGGCAATGAC       +174

TGGAACAAAG CCTATAAAAA ATCTGCCCGT GTCGTTGGTG ACGTAATCGG       +224

TAAATACCAT CCCCATGGTG ACTCGGCGGT CTATGACACG ATTGTCCGCA       +274

TGGCGCAGCC ATTCTCGCTG CGTTATATGC TGGTAGACGG TCAGGGTAAC       +324

TTCGGTTCTA TCGACGGCGA CTCTGCGGCG GCAATGCGTT ATACGGAAAT       +374

CCGTCTGGCG AAAATTGCCC ATGAACTGAT GGCCGATCTC GAAAAAGAGA       +424

CGGTCGATTT CGTTGATAAC TATGACGGCA CGGAAAAAAT TCCGGACGTC       +474

ATGCCAACCA AAATTCCTAA CCTGCTGGTG AACGGTTCTT CCGGTATCGC       +524

CGTAGGTATG GCAACCAACA TCCCGCCGCA CAACCTGACG GAAGTCATCA       +574

ACGGTTGTCT GGCGTATATT GATGATGAAG ACATCAGCAT TGAAGGGCTG       +624

ATGGAACACA TCCCGGGGCC GGACTTCCCG ACGGCGGCAA TCATTAACGG       +674

TCGTCGCGGT ATTGAAGAAG CTTACCGTAC CGGTCGCGGC AAGGTGTATA       +724

TCCGCGCTCG CGCAGAAGTG GAAGTTGACG CCAAAACCGG TCGTGAAACC       +774

ATTATCGTCC ACGAAATTCC GTATCAGGTA AACAAAGCGC GCCTGATCGA       +824

GAAGATTGCG GAACTGGTAA AAGAAAAACG CGTGGAAGGC ATCAGCGCGC       +874

TGCGTGACGA GTCTGACAAA GACGGTATGC GCATCGTGAT TGAAGTGAAA       +924

CGCGATGCGG TCGGTGAAGT TGTGCTCAAC AACCTCTACT CCCAGACCCA       +974

Forward-2    5'ATGCGG TCGGTGAAGT TGTGCT3''3C TTGGAGATGA GGGTCTGGGT

GTTGCAGGTT TCTTTCGGTA TCAACATGGT GGCATTGCAC CATGGTCAGC      +1024

C'5 Reverse-1

CGAAGATCAT GAACCTGAAA GACATCATCG CGGCGTTTGT TCGTCACCGC      +1074

CGTGAAGTGG TGACCCGTCG TACTATTTTC GAACTGCGTA AAGCTCGCGA      +1124

TCGTGCTCAT ATCCTTGAAG CATTAGCCGT GGCGCTGGCG AACATCGACC      +1174

CGATCATCGA ACTGATCCGT CATGCGCCGA CGCCTGCAGA AGCGAAAACT      +1224

GCGCTGGTTG CTAATCCGTG GCAGCTGGGC AACGTTGCCG CGATGCTCGA      +1274
```

```
                                             -continued
ACGTGCTGGC GACGATGCTG CGCGTCCGGA ATGGCTGGAG CCAGAGTTCG           +1324

GCGTGCGTGA TGGTCTGTAC TACCTGACCG AACAGCAAGC TCAGGCGATT           +1374

CTGGATCTGC CTTTGCAGAA ACTGACCGGT CTTGAGCACG AAAAACTGCT           +1424

CGACGAATAC AAAGAGCTGC TGGATCAGAT CGCGGAACTG TTGCGTATTC           +1474

TTGGTAGCGC CGATCGTCTG ATGGAAGTGA TCCGTGAAGA GCTGGAGCTG           +1524

GTTCGTGAAC AGTTCGGTGA CAAACGTCGT ACTGAAATCA CCGCCAACAG           +1574

CGCAGACATC AACCTGGAAG ATCTGATCAC CCAGGAAGAT GTGGTCGTGA           +1624

CGCTCTCTCA CCAGGGCTAC GTTAAGTATC AGCCGCTTTC TGAATACGAA           +1674

GCGCAGCGTC GTGGCGGGAA AGGTAAATCT GCCGCACGTA TTAAAGAAGA           +1724

AGACTTTATC GACCGACTGC TGGTGGCGAA CACTCACGAC CATATTCTGT           +1774

GCTTCTCCAG CCGTGGTCGC GTCTATTCGA TGAAAGTTTA TCAGTTGCCG           +1824

GAAGCCACTC GTGGCGCGCG CGGTCGTCCG ATCGTCAACC TGCTGCCGCT       +1874

Forward-3  5'TGCCGCT

GGAGCAGGAC GAACGTATCA CTGCGATCCT GCCAGTGACC GAGTTTGAAG   +1924

GGAGCAGGAC GAA3'          '3TAGGA CGGTCACTGG CTCAAAC'5    Reverse-2

AAGGCGTGAA AGTCTTCATG GCGACCGCTA ACGGTACCGT GAAGAAAACT           +1974

GTCCTCACCG AGTTCAACCG TCTGCGTACC GCCGGTAAAG TGGCGATCAA           +2024

ACTGGTTGAC GGCGATGAGC TGATCGGCGT TGACCTGACC AGCGGCGAAG           +2074

ACGAAGTAAT GCTGTTCTCC GCTGAAGGTA AAGTGGTGCG CTTTAAAGAG           +2124

TCTTCTGTCC GTGCGATGGG CTGCAACACC ACCGGTGTTC GCGGTATTCG           +2174

CTTAGGTGAA GGCGATAAAG TCGTCTCTCT GATCGTGCCT CGTGGCGATG           +2224

GCGCAATCCT CACCGCAACG CAAAACGGTT ACGGTAAACG TACCGCAGTG           +2274

GCGGAATACC CAACCAAGTC GCGTGCGACG AAAGGGGTTA TCTCCATCAA           +2324

GGTTACCGAA CGTAACGGTT TAGTTGTTGG CGCGGTACAG GTAGATGACT           +2374

GCGACCAGAT CATGATGATC ACCGATGCCG GTACGCTGGT ACGTACTCGC           +2424

GTTTCGGAAA TCAGCATCGT GGGCCGTAAC ACCCAGGGCG TGATCCTCAT           +2474

CCGTACTGCG GAAGATGAAA ACGTAGTGGG TCTGCAACGT GTTGCTGAAC           +2524

CGGTTGACGA GGAAGATCTG GATACCATCG ACGGCAGTGC CGCGGAAGGG          +2574

GACGATGAAA TCGCTCCGGA AGTGGACGTT GACGACGAGC CAGAAGAAGA           +2624

ATAATTTTAC TTCTTCATGC CAAAAGGGAG CTATCTCCCT TGTTTGAATT   +2674

'3TAGAGGGA ACAAACTTAA

GAAAAGTCCA GGCTGCAAAG TCTGGGCTTT TGTCGTATTA GGGCACGGTA     +2724

CT'5 Reverse-3

AAGTTTGGCT GTGCCCGTAA AAAATGGCTG GCTATACACA AGGAATGTGG           +2774

CAATGAGTGG TGAAAAAAAG GCGAAAGGCT GGCGGTTCTA TGGTCTTGTA           +2824

GGTTTTGGCG CAATAGCACT GCTTTCCGCT GGCGTCTGGG CGTTGCAATA           +2874
```

```
TGCTGGCAGT GGGCCAGAAA AAACGTTGTC GCCGCTGGTG GTGCACAACA        +2924

ATCTGCAAAT CGATCT                                            +2940
```

Size of the gyr A Gene 2628 Bases

Using the primer pair as mentioned below of SEQ ID No. 3 and 4 respectively, 1023 base pair sequence was amplified and sequenced (−48 to +975).

```
Forward-1 5'A ATTTGCGACC TTTGAATCCG 3'    (21 bases)

Reverse-1 5'CTGGGTCTGGGAGTAGAGGTTG 3'     (22 bases)
```

Using the primer pair SEQ ID No. 5 and 6 respectively as mentioned below 993 base pair sequence was amplified and sequenced (−929 to +1921).

```
Forward-2 5'ATGCGGTCGGTGAAGTTGTGCT 3'    (22 bases)

Reverse-2 5'CAAACTCGGTCACTGGCAGGAT 3'    (22 bases)
```

Using the primer pair SEQ ID No. 7 and 8 respectively as mentioned below 809 base pair sequence was amplified and sequenced (+1868 to 2676).

```
Forward-2   5'TGCCGCTGGAGCAGGACGAA 3'    (20 bases)

Reverse-2   5'TCAATTCAAACAAGGGAGAT 3'    (20 bases)
```

Using these primers the total gyrase A gene was amplified to three fragments separately, purified and sequenced in AB1 prism 377 automatic DNA sequencer. The sequences of the mutants were compared to the wild type.

Development of α-arteether Resistant Mutant from α-arteether Sensitive Mutants:

In order to develop an arteether resistant mutants from an arteether sensitive strains a reverse strategy was applied. Quinoline/fluoroquinolone (Q/FQs) resistant strains were developed spontaneously i.e. screening overnight log phase culture of the Quinolone/fluoroquinolone sensitive i.e. arteether resistant strain (*E coli* CA 8000) on the poison agar plate of the Q/FQs. The Q/FQ resistant mutants which appeared on the poison agar plates were first purified through single colony purification and then checked for their arteether sensitivity. These arteether sensitive mutants on the contrary when checked for their Q/Fqs resistance they show different level of Q/FQs resistance.

Bioactivity of Beta-arteether on Selected Q/FQr Mutants Compared to *E. coli* CA 8000:

The strains of *E coli* mutants were grown on Luria agar medium and beta-arteether (250 μg/disc) was applied on disc. The clear zone around the disc killing the bacteria is called Zone of Inhibition (ZOI). This is the measure of sensitivity of the strain towards the compound alpha-arteether.

TABLE 1

| Strains of *E. coli*/Mutants | Net ZOI in mm (250 μg/disc) |
|---|---|
| CA8000 (gyrA+) | — |
| DH5 αgyrA−) | 5 |
| ET8000 (gyrA−) | 5 |
| NK5819 (gyrA−) | 7 |
| CA8001 | 10 |
| CA8002 | 5 |
| CA8003 | 9 |
| CA8006 | 11 |
| CA8007 | 8 |
| CA8009 | 14 |
| CA8010 | 10 |
| CA8012 | 8 |

Level of Cross Resistance of Different Mutants Compared to *E. coli* CA 8000:

The minimum inhibitory concentrations (MIC) of the quinolone and fluoroquinolone antibiotics were quantified for different strains and compared among each other. The differential response indicate the measure of resistance and sensitivity. Higher MIC indicate more resistance.

TABLE 2

| Mutant Strains | Nalidixic acid μg/ml | Norfloxacin μg/mL | Sparfloxacin μg/ml | Ciprofloxacin μg/ml | Lomefloxacin μg/ml |
|---|---|---|---|---|---|
| CA8000 | 2.0 | <0.05 | <0.05 | <0.05 | <0.05 |
| DH5a | 50 | 20 | 10 | 0.1 | 0.5 |
| ET8000 | 100 | 50 | 20 | 0.5 | >2.0 |
| NK5819 | 20 | 25 | 10 | <0.1 | <0.5 |
| CA8001 | 150 | 15 | 20 | <0.1 | 1.5 |
| CA8002 | 150 | 15 | 20 | <0.1 | 1.5 |
| CA8003 | 150 | 15 | 20 | <0.1 | 2.5 |
| CA8005 | 150 | 10 | 20 | 0.1 | 0.5 |
| CA8006 | 150 | 20 | 40 | 0.1 | 1.5 |
| CA8007 | 100 | 15 | 20 | 0.1 | 1.5 |
| CA8009 | 100 | 15 | 40 | 0.1 | 1.5 |
| CA80010 | 100 | 15 | 40 | 0.1 | 1.5 |
| CA80012 | 100 | 15 | 40 | 0.1 | 1.5 |

Phenotypic as well as Genotypic Characteristics of the Mutants:

The strains of E coli of the investigation, their phenotypes in terms of a-arteether (resistance or sensitivity, superscript R or S) or antibiotic resistance or sensitivity, change in nucleotide position of the gyrase A gene leading to the phenotype, corresponding amino acid change in the protein and the position of amino acid change are being described. Always the phenotype a-arteether resistance is accompanied with quinolone or fluoroquinolone sensitivity and vice versa.

The α-arteether resistance domain(ARD) can be defined as the domain from 241 nucleotide position to 261 nucleotide position of gyr A gene from the translation start site (ATG codon) of *Escherichia coli* corresponding to 81 to 87 amino acid position in the gyrase A peptide of the enzyme from the N-terminal end. The N-terminal end can be defined as the starting amino acid in the peptide.

The ARD may extend further beyond the above mentioned nucleotide positions on either direction of the range men-

TABLE 3

| S. No | E. coli Strains | Phenotype | Change in nucleotide (Position) | Change in Aminoacid | Position of changed Aminoacid |
|---|---|---|---|---|---|
| 1 | DH5α | a-arteether$^S$/Nal$^R$ | GAC-----AAC(259) | Asp-----Asn. | 87 |
| 2 | ET8000 | a-arteether$^S$/Nal$^R$ | GAC-----AAC(259) | Asp-----Asn. | 87 |
| 3 | NK5819 | a-arteether$^S$/Nal$^R$ | GAC-----TAC(259) | Asp-----Gly | 87 |
| 4 | CA8001 | a-arteether$^S$/Nal$^R$ Mutant | GGT-----TGT(241) | Gly-----Cys | 81 |
| 5 | CA8002 | a-arteether$^S$/Nal$^R$ Mutant | GGT-----TGT(241) | Gly-----Cys | 81 |
| 6 | CA8003 | a-arteether$^S$/Nal$^R$ Mutant | GAC-----GGC(260) | Asp-----Gly | 87 |
| 8 | CA8005 | a-arteether$^S$/Nal$^R$ Mutant | GAC-----GGC(260) | Asp-----Gly | 87 |
| 9 | CA8006 | a-arteether$^S$/Nal$^R$ Mutant | TCG-----TTG(248) | Ser-----Leu | 83 |
| 10 | CA8007 | a-arteether$^S$/Nal$^R$ Mutant | TCG-----TTG(248) | Ser-----Leu | 83 |
| 12 | CA8009 | a-arteether$^S$/Nal$^R$ Mutant | TCG-----TTG(248) | Ser-----Leu | 83 |
| 13 | CA8010 | a-arteether$^S$/Nal$^R$ Mutant | TCG-----TTG(248) | Ser-----Leu | 83 |
| 15 | CA8012 | a-arteether$^S$/Lome$^R$ Mutant | GGT-----GAT(242) | Gly-----Asp. | 81 |

Phenotypic as well as Genotypic Characters (gyr A Gene, QRDR Region) of the WT as well as Revertants:

The commercially available strain E. coli DH5□ (Stratagene, USA) is sensitive to □-arteether but resistant to quinolone/fluoroquinolone due to a mutation at 87$^{th}$ aminoacid position of the gyr A protein (Aspartic acid of wild type is changed to Aspargine) with corresponding change in the codon GAC to AAC. This strain was used to screen □-arteether resistant mutations. The observation was startling as the □-arteether resistant mutants are the exact reversion at the 87$^{th}$ position of the aminoacid of gyrase A subunit i.e. Aspargine changed to aspartic acid, with corresponding change in the codon AAC to GAC. Similarly When the mutants (a-arteether$^S$/Lom$^R$) were searched for a-arteether sensitivity those were found to be exact revertants at aminoacid position 81.

tioned and not limited to *Escherichia coli* only as the gyr. A gene is highly conserved among different bacterial species.

The commercially available strain *E.coli* DH5α (Stratagene, USA) is sensitive to α-arteether but resistant to quinoline/fluoroquinolone due to a mutation at 87$^{th}$ aminoacid position of the gyr A protein (Aspartic acid of wild type is changed to Aspargine) with corresponding change in the codon GAC to AAC. This strain was used to screen α-arteether resistant mutations. The observation was starting as the α-arteether resistant mutants are the exact reversion at the 87$^{th}$ position of the amino acid of gyrase A subunit i.e. Aspargine changed to Aspartic acid, with corresponding change in the codon AAC to GAC.

TABLE 4

| S. No | E. coli Mutant Strains | Phenotype | Change in nucleotide | Change in Aminoacid | Position of changed Aminoacid |
|---|---|---|---|---|---|
| 2 | AR 9 CA8014 | a-arteether$^R$/Nal$^S$ Mutant | AAC-----GAC(259) | Asn.-----Asp | 87 |
| 3 | Rev. 1 | a-arteether$^R$/Lom$^S$ Mutant | GAT-----GGT(242) | Asp-----Gly | 81 |
| 4 | Rev. 2 | a-arteether$^R$/Lom$^S$ Mutant | GAT-----GGT(242) | Asp-----Gly | 81 |
| 5 | Rev. 3 | a-arteether$^R$/Lom$^S$ Mutant | GAT-----GGT(242) | Asp-----Gly | 81 |
| 6 | Rev 4 | a-arteether$^R$/Lom$^S$ Mutant | GAT-----GGT(242) | Asp-----Gly | 81 |
| 7 | Rev 5 | a-arteether$^R$/Lom$^S$ Mutant | GAT-----GGT(242) | Asp-----Gly | 81 |
| 8 | Rev 6 | a-arteether$^R$/Lom$^S$ Mutant | GAT-----GGT(242) | Asp-----Gly | 81 |

45

The invention claimed is:

1. An isolated oligonucleotide consisting of alpha-arteether resistance conferring domain (ADR) of SEQ